United States Patent [19]

Fory et al.

[11] 4,105,685
[45] Aug. 8, 1978

[54] AGENT FOR THE REGULATION OF PLANT GROWTH

[75] Inventors: Werner Fory, Basel; Hanspeter Fischer, Bottmingen, both of Switzerland

[73] Assignee: Ciba-Geigy Corporation, Ardlsey, N.Y.

[21] Appl. No.: 503,429

[22] Filed: Sep. 5, 1974

Related U.S. Application Data

[63] Continuation-in-part of Ser. No. 336,572, Feb. 28, 1973, abandoned.

[30] Foreign Application Priority Data

Mar. 2, 1972 [CH] Switzerland .......................... 3048/72

[51] Int. Cl.$^2$ ............................. C07F 7/10; C07F 7/18; C07F 7/08
[52] U.S. Cl. ................................ 260/448.2 N; 71/79; 71/98; 71/121; 260/448.8 R
[58] Field of Search .................. 260/448.2 N, 448.8 R

[56] References Cited

U.S. PATENT DOCUMENTS 3,928,406  12/1975  Leeper et al. ................. 260/448.8 R Primary Examiner—Paul F. Shaver
Attorney, Agent, or Firm—Harry Falber

[57] ABSTRACT

The present invention relates to new compositions and methods for the regulation of plant growth, especially for fruit and leaf abscission, acceleration of ripening and latex discharge in rubber trees and to new active substances of the class of β-halogenoethyl-silanes.

The active substances of the new compositions correspond to the formula

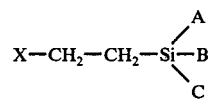

wherein X is chlorine or bromine, A represents a radical —$SR_1$ or —$NR_2R_3$, B represents a radical —$SR_1$, —$NR_2R_3$ or —$OR_4$, and C represents a radical —$SR_1$, —$NR_2R_3$, —$OR_4$ or the methyl or benzyl group. The symbols $R_1$ to $R_4$ are chosen from substituted or unsubstituted alkyl, alkenyl, alkynyl, cycloalkyl, cycloalkenyl, phenyl and benzyl groups, $R_2$ can also be hydrogen and $R_2$ together with $R_3$ and the adjacent nitrogen can form a heterocyclic ring system.

14 Claims, No Drawings

AGENT FOR THE REGULATION OF PLANT GROWTH

CROSS-REFERENCE TO RELATED APPLICATION

This application is a continuation-in-part of our application Ser. No. 336,572, filed Feb. 28, 1973, now abandoned.

DETAILED DISCLOSURE

The present invention relates to new compositions and methods for the regulation of plant growth by the use of new β-halogenoethyl-silanes as active substances, also to new β-halogenoethyl-silanes and to processes for the production of these silanes.

The β-halogenoethyl-silanes contained as active substances in the new agents correspond to formula I

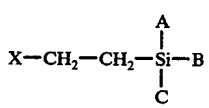
(I)

The symbols in this formula have the following meanings:

X represents chlorine or bromine,
A represents a radical —S—R$_1$ or

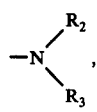

B represents a radical —S—R$_1$,

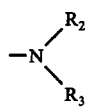

—OR$_4$, and
C represents a radical —S—R$_1$,

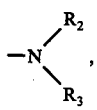

—OR$_4$ the methyl or benzyl group.

The symbols R$_1$, represents alkyl radicals, alkyl radicals substituted by alkoxycarbonyl, phenyl, cycloalkyl or heterocyclic radicals, as well as alkenyl, alkynyl, cycloalkyl and cycloalkenyl radicals; phenyl radicals optionally mono- or polysubstituted by alkyl, alkoxy, alkylthio and/or halogen; and benzyl radicals optionally mono- or polysubstituted by alkyl, alkoxy, alkylthio and/or halogen.

The symbol R$_3$ represents alkyl which can be substituted by alkoxy, alkylthio, phenyl, cycloalkyl, or by a heterocyclic radical; also cycloalkyl, cycloalkenyl, alkenyl, alkynyl; phenyl optionally mono- or poly-substituted by alkyl, alkoxy, alkylthio and/or halogen; and benzyl optionally mono- or polysubstituted by alkyl, alkoxy, alkylthio and/or halogen.

The symbol R$_2$ represents hydrogen or the same as R$_3$, whereby R$_2$ and R$_3$ together with the adjacent nitrogen atom can however also form a saturated ring system.

The symbol R$_4$ represents alkyl radicals; alkyl radicals substituted by halogen, alkoxy, alkanoyloxy, aroyloxy, aryloxy, alkoxyalkoxy, alkenyloxy, phenoxy, cycloalkyl, alkylthio and/or alkoxycarbonyl; alkenyl or halogenoalkenyl, alkynyl, cycloalkyl, cycloalkenyl; phenyl radicals optionally mono- or poly-substituted by cyano, nitro, alkyl, halogenoalkyl, alkoxy, alkylthio, alkanoyl and/or alkoxycarbonyl; and benzyl radicals optionally mono- or poly substituted by allyl, alkoxy and/or halogen.

The β-halogenoethyl silanes of formula I can be divided into the following groups:

(a) compounds, wherein A = B = C = —S—R$_1$ of the formula Ia

(Ia);

(b) compounds wherein A = B = —S—R$_1$ and C is methyl of the formula Ib

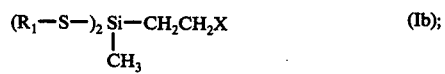
(Ib);

(c) compounds wherein A = B = SR$_1$ and C = —O—R$_4$ of the formula Ic

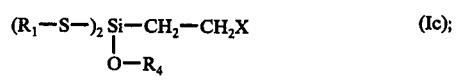
(Ic);

(d) compounds wherein A = —S—R$_1$ and B = C = —O—R$_4$ of the formula Id

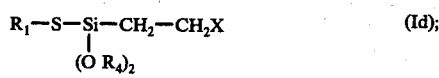
(Id);

(e) compounds wherein A = —S—R$_1$, B = —O—R$_4$ and C is methyl of the formula Ie

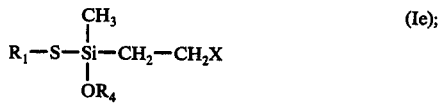
(Ie);

(f) compounds wherein A = B = C =

of the formula If

(If);

(g) compounds wherein A = B =

and C is methyl of the formula Ig

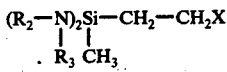

(h) compounds wherein A=

B = —O—R$_4$ and C is methyl or benzyl of the formula Ih

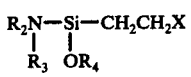

In the formulae Ia - Ih the substituents R$_1$ - R$_4$ have the meaning given under formula I and R$_5$ is a methyl or benzyl radical.

By alkyl radicals are meant straight-chain or branched radicals having 1 to 18 carbon atoms, such as, e.g. methyl, ethyl, n-propyl, isopropyl, n-butyl, sec-butyl, n-hexyl, n-octyl, n-dodecyl, n-octadecyl, and so forth. It is particularly the straight-chain and branched alkyl radicals having 1 to 8 carbon atoms which form the alkyl moiety of alkoxy, alkylthio or alkoxycarbonyl substituents of an alkyl radical or of a phenyl radical, In the case of halogenoalkyl radicals, these are alkyl radicals having 1 to 6 carbon atoms, which can be substituted by fluorine, chlorine and/or bromine, such as, e.g. trifluoromethyl, 2-chloroethyl, 6-chlorohexyl, etc. Alkenyl radicals are straight-chain or branched radicals having 3 to 18 carbon atoms, e.g. propenyl, butenyl, octenyl, decenyl or heptadecenyl radicals.

These alkenyl radicals can be mono- or polysubstituted by halogen, such as fluorine, chlorine, bromine and/or iodine. Alkenyl radicals having 3 to 6 carbon atoms form the alkenyl moiety of alkenyloxy radicals. Alkynyl radicals preferably contain 3 to 8 carbon atoms in a straight chain, such as, e.g. 2-propynyl, 2-butynyl or 3-hexynyl. By cycloalkyl and cycloalkenyl radicals are meant mono- and polycyclic radicals having 3 to 12 carbon atoms, such as, e.g. cyclopropyl, cyclopentyl, cyclopentenyl, cyclohexyl, cyclohexenyl or bicycloheptyl, etc.

The β-halogenoethyl-silanes of formula I affect in a varying manner the growth of parts of plants above and below the soil, and have a low toxicity towards warm-blooded animals. The active substances cause no morphological changes or damage which would result in the withering of the plant. The compounds are not mutagenic. Their action differs from that of a herbicidal active substance and of a fertiliser. The action corresponds more to the effects which can be observed on application of ethylene to various parts of plants. It is known that the plant itself produces, in various stages of development, ethylene to a varying degree, particularly before and during the ripening process of the fruits, and at the end of the vegetation period with the occurring abscission of fruit and leaves. Since the regulation of ripening and of fruit and leaf abscission by application of chemical substances is of the greatest commercial importance in the cultivation of fruit, citrus fruit, pineapples and cotton, efforts have been directed towards the discovery of compounds with which such effects might be obtained, without the treated plants suffering any kind of damage in the process. Thus, various classes of substances have meanwhile become known with which it has been possible to obtain some of the growth-regulating effects referred to; however, the extent of the range of action of these substances corresponds in no way to that of ethylene. Compounds which under certain conditions release ethylene are known. Such compounds have the disadvantage either in that they are relatively unstable under the influences of weather, because they are very susceptible to hydrolysis, or in that they are phytotoxic. In the South African Pat. Specification No. 68/1036, β-halogenoethyl-phosphonic acid derivatives are described as active substances which regulate plant growth. These compounds decompose in and on the plant with the release of ethylene, and are therefore similar in action and range of action to ethylene. By virtue of their very low stability, phosphonic acid derivatives are not able, however, to satisfy the demands made on them. As they are stable only in an acid medium, more precisely in a pH-range below 5, the active-substance concentrates have to be stabilised by the addition of acids. This addition of acid however, limits the range of application of these active substances in view of the resulting phytotoxic effects. Furthermore, the storage of such sensitive concentrates of active substance presents difficulties.

Further compounds known as herbicidal active substances are halogenoalkyl-methyl-silanes [cp. U.S. Pat. Nos. 3,390,976 and 3,390,977, and J. K. Leasure et al., J. Med. Chem. 9, 949 (1966) ]. β-Chloroethylmethyl-dimethoxysilane was produced by J. K. Leasure et al. (loc.cit), but has no herbicidal action. The U.S. Pat. No. 3,183,076 describes α-chloroethylmethyl-dialkoxysilanes, which can be used for the promotion of germination power, leaf abscission, etc.

The present invention relates to new agents containing as active substances β-halogenoethyl-silanes, which have a stimulating or retarding action on plant growth in the various stages of development of the plants. These agents can contain the usual carrier substances, distributing agents, and stabilisers protecting against the effects of light and of oxidation. The action of the new agents is to regulate vegetative plant growth and germination power, and to promote the formation of blossom, the development of fruit and the growth of abscission layers. In the case of monocotyledons, an increase in tillering and branching was observed with a simultaneous reduction of growth in height. There was moreover a strengthening of the support tissues of the stalks in the case of the treated plants. The formation of undesirable side shoots on various types of plants is very greatly reduced; for example, the vegetative growth of grape vines is inhibited. The new compounds also have a secretion-promoting action; for example, the latex discharge in the case of Hevea brasiliensis is promoted, an effect which is of great commercial importance. As tests have shown, the rooting of seedlings and cuttings, as well as the development of tubers in the case of potatoes, is promoted. In addition, there occurs a simultaneous sprouting of dormant rhizomes, a factor which is particularly important concerning the various perennial weeds, such as couchgrass, Johnson grass and cyperus, for these can then be easily destroyed or suppressed by herbicides. The germination capacity of seeds, such as, e.g. seed potatoes and legumes, is promoted with low concentrations, and inhibited with higher concentrations. Both the one effect and the other can be commercially important. A regulation of the blossoming time and of the number of blossoms is possible in the case of many ornamental and cultivated plants. This effect is a particularly important factor in the growing of pineapples. If all the trees or shrubs blossom at the same time, then the crops can be gathered within a comparatively short space of time. With regard to cucurbitaceae, there occurs a displacement of the blossom sex differentiation in favour of pistillate flowers.

Tests have shown that in the case of fruit trees there occurs a thinning of blossom and fruit. Furthermore, fruit ripening and fruit colouration are accelerated and improved, e.g. with oranges, melons, apricots, peaches, tomatoes, bananas, bilberries, figs, coffee, pepper, tabacco and pineapples. As a result of the development of abscission layers, the abscission of fruit and leaves is rendered appreciably more easy. This factor has great commercial significance with regard to mechanical harvesting, e.g. of citrus fruits, such as oranges, grapefruits and olives; or stone fruit such as cherries, damsons, peaches, plums and apricots; or pomaceous fruit such as apples and pears; or soft fruit such as currants, rasberries and bilberries; or nuts such as walnuts and pecan nuts; or sub-tropical fruits such as coffee, figs and pepper, or cotton. With high concentrations, the defoliation of ornamental plants, such as chrysanthemums, rhododendrons, carnations and roses, is also obtained.

The extent and the nature of the action are dependent on the most diverse factors; they are dependent particularly on the time of application with regard to the stage of development of the plant, and on the application concentration. These factors vary, however, depending on the type of plant and on the effect desired. Thus, for example, lawns are treated during the entire growth period; ornamental plants, of which, e.g. the intensity and number of the blossoms are to be increased, before development of the blossom setting; plants of which the fruit is to be sold, or in some other way utilised, immediately after blossoming, or at an appropriate interval of time before the gathering of the crop. Application of the active substances is effected by the use of solid or liquid agents, these being applied to parts of plants above the soil, to the surface of the soil, as well as into the soil itself. The preferred method is the application to the parts of plants above the soil, for which purpose solutions or aqueous suspensions are most suitable. In addition to solutions and dispersions for the treatment of the growth substrate (soil), dusts, granulates and scattering agents are also suitable.

The essential promotion of the abscission of citrus fruits and bean leaves with the use of agents according to the invention was demonstrated by the following tests.

The active substances are sprayed, in the form of solutions in concentrations of 0.2% and 0.4%, respectively, onto branches, well hung with fruit, of various orange trees. The tests are evaluated after 14 days according to the method developed by W. C. Wilson and C. H. Hendershott [Proc. Am. Soc. Hort. Sc. 90, 123 - 129 (1967)]. The test consists in the measuring of the force in kilograms required to effect the abscission of the fruit.

In the case of bean-leaf abscission tests, segments of bean leaves of the type "Tempo" are immersed in a solution of 0.002% of active substance; for each active substance, 4–8 segments are left for 6 days in the active substance solution under controlled conditions. On specific days after commencement of the treatment, the number of resulting abscissions (contraction or necking of the stalk in the abscission zone on the leaf-side) is assessed.

Tests with agents containing the following active substances produced excellent results in both tests:
  2-chloroethyl-(dibenzylthio-hexyloxy)-silane, No. 33
  2-chloroethyl-(benzylthio-dihexyloxy)-silane, No. 48
  2-chloroethyl-(methyl-benzylthio-benzyloxy)-silane, No. 75
  2-chloroethyl-(methyl-dibenzylamino)-silane, No. 109
  2-chloroethyl-(methyl-dioctylamino)-silane, No. 89
  2-chloroethyl-(methyl-benzyloxy-butylthio)-silane, No. 66
  2-chloroethyl-(dibutylthio-hexyloxy)-silane, No. 28
  2-chloroethyl-(butylthio-dihexyloxy)-silane. No. 57a 70 to 100% of all leaves treated with these compounds showed, after six days, contraction or necking of the stalk in the abscission zone of the leaf-side.

If the branches of olive trees are treated until dripping wet with a 0.4% solution of 2-chloroethyl-(methyl-dioctylamino)-silane, then after a period of seven days 50 to 75% of the olives, depending on the variety, are caused to fall by a shaking of the treated branches.

Agents according to the invention are produced in a manner known per se by the intimate mixing and grinding of active substances of the general formula I with suitable carriers, optionally with the addition of dispersing agents or solvents which are inert to the active substances.

Water-dispersible concentrates of active substance, i.e. wettable powders, pastes and emulsion concentrates, are active substance concentrates which can be diluted with water to obtain any desired concentration. They consist of active substance, carrier, optionally additives which stabilise the active substance, surface-active substances, and anti-foam agents and, optionally, solvents. The concentration of active substance in these agents is 0.5 - 80%.

The wettable powders and pastes are obtained by the mixing and grinding of the active substances with dispersing agents and pulverulent carriers, in suitable devices, until homogeneity is attained. Suitable carriers are, e.g. the following: kaolin, talcum, bole, loess, chalk, limestone, ground limestone, Attaclay, dolomite, diatomaceous earth, precipitated silicic acid, alkaline-earth metal silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Suitable dispersing agents are, e.g. the following: condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, dialkyldilaurylammonium chloride and fatty acid alkali metal and alkaline-earth metal salts.

Suitable anti-foam agents are for example silicones.

To these mixtures may also be added additives stabilising the active substance, and/or non-ionic, anion-active and cation-active substances, which, for example, improve the adhesiveness of the active substances on plants and on parts of plants (adhesives and agglutinants), and/or ensure a better wettability (wetting agents). Suitable adhesives are, for example, the following: olein/lime mixture, cellulose derivatives (methyl cellulose, carboxymethyl cellulose), hydroxyethylene glycol ethers of mono- and dialkylphenols having 5 - 15 ethylene oxide radicals per molecule and 8 - 9 carbon atoms in the alkyl radical, ligninsulphonic acid, alkali metal and alkaline-earth metal salts thereof, polyethylene glycol ethers (carbowaxes), fatty alcohol polyglycol ethers having 5 - 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea/formaldehyde, as well as latex products. The active substances are so mixed, ground, sieved and strained with the above mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g. the following: ketones, benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances) of the general formula I is (or are) dissolved in suitable organic solvents, solvent mixtures, or water. The following can be used as organic solvents: aliphatic and aromatic hydrocarbons, chlorinated derivatives thereof, alkylnaphthalenes, or mineral oils on their own or in admixture with each other. The solutions should contain the active substances in a concentration range of from 1 to 20%.

The solid preparations, such as dusts, scattering agents and granulates, contain solid carriers such as those mentioned in the foregoing, and, optionally, additives stabilising the active substance. The particle size of the carriers is for dusts advantageously up to about 0.1 mm; for scattering agents from about 0.075 mm to 0.2 mm; and for granulates 0.2 mm or coarser. The concentrations of active substance in the solid preparations are from 0.5 to 80%.

All the mentioned active substance concentrates may also contain agents stabilising against the effects of light, and antioxidants.

In the following are described several types of preparations containing active substances usable according to the invention. Where not otherwise stated, the term 'parts' denotes parts by weight.

GRANULATE

The following substances are used for the preparation of a 5% granulate:
 5 parts of 2-chloroethyl-(benzylthio-dihexyloxy)-silane,
 0.25 parts of epichlorohydrin,
 0.25 parts of cetyl polyglycol ether,
 3.50 parts of polyethylene glycol ("carbowax"),
 91 parts of kaolin (particle size 0.2 - 0.8 mm).

The active substance is mixed with epichlorohydrin and the mixture dissolved in 6 parts of acetone; to the solution are then added polyethylene glycol and cetyl polyglycol ether. The thus obtained solution is sprayed on to kaolin, and the acetone subsequently evaporated in vacuo.

WETTABLE POWDER

The following constituents are used for the preparation of (a) a 40%, (b) a 50%, (c) a 25%, and (d) a 10% wettable powder:
 (a) 40 parts of 2-chloroethyl-(dibenzylthio-hexyloxy)-silane,
  5 parts of sodium lignin sulphonate,
  1 part of sodium dibutyl-naphthalene sulphonate,
  54 parts of silicic acid;
 (b) 50 parts of 2-chloroethyl-(methyl-dioctadecylamino)-silane,
  5 parts of alkylaryl sulphonate ("Tinovetin B"),
  10 parts of calcium lignin sulphonate,
  1 part of Champagne chalk/hydroxyethyl cellulose mixture (1 : 1),
  20 parts of silicic acid,
  14 parts of kaolin;
 (c) 25 parts of 2-chloroethyl-(methyl-benzylthio-benzyloxy)-silane,
  5 parts of the sodium salt of oleylmethyl tauride,
  2.5 parts of naphthalenesulphonic acid/formaldehyde condensate,
  0.5 parts of carboxymethyl cellulose,
  5 parts of neutral potassium aluminium silicate,
  62 parts of kaolin;
 (d) 10 parts of 2-chloroethyl-(benzylthio-di-hexyloxy)-silane,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives; the mixture is subsequently ground in suitable mills and rollers. Wettable powders are thus obtained which can be diluted with water to give suspensions of any desired concentration. Such suspensions are employed, e.g. for the removal of undesired side shoots, for the tillering of lawns, and for the rooting of seedlings and cuttings, etc.

EMULSION CONCENTRATE

The following constituents are mixed together to produce 25% emulsion concentrates:
 (a) 25 parts of 2-chloroethyl-(methyl-benzylthio-benzyloxy)-silane,
  5 parts of a mixture of nonylphenolpolyoxyethylene and calcium-dodecylbenzene sulphonate,
  70 parts of xylene;
 (b) 25 parts of 2-chloroethyl-(dibenzylthio-hexyloxy)-silane,
  10 parts of a mixture of nonylphenolpolyoxyethylene and calcium-dodecylbenzene sulphonate,
  65 parts of cyclohexanone.

This concentrate can be diluted with water to obtain emulsions of any desired concentrations. Such emulsions are suitable for the thinning out of blossom and fruit, for the accelerated ripening of fruits, and for the promotion of fruit and leaf abscission.

All β-halogenoethyl-silanes embraced by formula I are new compounds. The new β-halogenoethyl-silanes of formula I wherein C is not the methyl group are produced according to the present invention by the reaction of a β-halogenoethyl-trichloro-silane of formula II $$X-CH_2-CH_2-Si-Cl_3 \qquad (II)$$

with three equivalents freely chosen from one or more of the types of mercaptans, amines or alcohols of formulae III, IV or V.

$$R_1SH \qquad (III)$$

$$R_2R_3NH \qquad (IV)$$

$$R_4OH \qquad (V)$$

The new β-halogenoethyl-silanes of formula I where C represents methyl or benzyl are produced in an analogous manner by the reaction of a β-halogenoethyl-methyl-dichlorosilane of formula VI

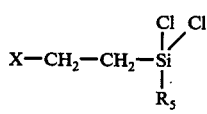

wherein $R_5$ is a methyl or benzyl radical, with one or two equivalents of one of the mercaptans, amines or alcohols of the formulae III, IV, V or V. In the formulae II to VI of the starting materials, X represents chlorine or bromine, and $R_1$, $R_2$, $R_3$, $R_4$ have the meanings given under formula I and $R_5$ represents a methyl or benzyl radical.

The process is preferably carried out in the presence of solvents and/or diluents which are inert to the reactants. Aprotic solvents are particularly suitable, such as, e.g. aliphatic and aromatic hydrocarbons, e.g. hexane, cyclohexane, benzene, toluene, xylene, halogenated hydrocarbons such as chlorinated ethylene, carbon tetrachloride, chloroform, chlorobenzene, also ethers and ethereal compounds such as diethyl ether, tetrahydrofuran, etc.

A complete reaction is obtained moreover where the alcohols, mercaptans or amines employed as reactants are used in excess to serve as solvents or diluents.

Furthermore, the addition of an acid-binding agent to the reaction mixture may be necessary in some cases. Suitable acid-binding agents for this purpose are, in particular, tertiary amines such as trialkylamines, e.g. triethylamine, pyridine and pyridine bases, dialkylanilines, etc.

The reaction temperatures are in the range of 0 to 100° C; the reaction duration can vary from a few minutes to several days, and depends to a great extent on the reactivity of the mercaptans, amines or alcohols employed.

The two starting materials of formula II wherein X represents chlorine or bromine are known. β-Chloroethyltrichloro-silane can be produced, for example, by reaction of ethyl-trichloro-silane with chlorine (cp. L. H. Sommer et al., J. Am. Chem. Soc. 68, 1881 (1946); and β-bromoethyltrichloro-silane by reaction of ethyl-trichloro-silane with bromine (K. W. Michael, J. Org. Chem. 34, 2832 (1969); or by HBr-addition to vinyl-trichloro-silane according to the method of A. I. Bourne (J. Chem. Soc., Sect. C. 1970, 1740). Catalysts which can be used for this addition reaction are UV-light, peroxides and radical initiators.

Of the two starting materials of formula IX, the chlorine compound wherein X represents chlorine is known, and can be produced, for example, by reaction of ethyl-(methyl-dichloro)silane with chlorine (cp. J. K. Leasure et al., loc. cit.).

The starting material of formula IX wherein X represents bromine has not hitherto been described in the literature.

β-Bromoethyl-methyl-dichloro-silane is produced by methods known per se by reaction of ethyl-(methyl-dichloro)-silane with bromine, corresponding to the process described by K. W. Michael (loc.cit.) for the production of β-bromoethyl-trichloro-silane; or by HBr-addition to vinyl-methyl-dichloro-silane analogously to the mode of reaction described by A. I. Bourne (loc. cit.). For these addition reactions the catalyst can be UV-light, peroxides and radical initiators.

Also known are halogenoalkyl-methyl-silanes as herbicidal active substances; cp. U.S. Pat. Nos. 3,390,976 and 3,390,977, and J. K. Leasure et al., J. Med. Chem. 9, 949 (1966).

The U.S. Pat. No. 3,183,076 describes α-chloroethyl-methyl-dialkoxy-silanes, which can be used for the promotion of germination and leaf-abscission, etc.

The following examples serve to further illustrate the process according to the invention. In the attached table there are listed further β-halogenoethyl-silanes of formula I produced by the methods described in the examples.

The temperatures are expressed in degrees Centigrade.

EXAMPLE 1 (Production of an intermediate)

An amount of 59.4 g of 2-chloroethyl-trichlorosilane is dissolved in 750 ml of absolute diethyl ether; an addition is then made in the course of one hour at $-5°$ to $-10°$ of a mixture of 34.9 g of hexan-(1)-ol and 23.7 g of absolute pyridine dissolved in 250 ml of absolute ether. The mixture is afterwards stirred for 12 hours at room temperature; filtration is then performed and the filtrate concentrated in vacuo. After fractional distillation there is obtained 39.2 g of 2-chloroethyl-(hexyloxy-dichloro)-silane;

B.P.: 69°- 72°/0.1 Torr.

Calculated: C, 36.5; H, 6.5; Si, 10.7%. Found: C, 36.5; H, 6.5; Si, 11.0%.

EXAMPLE 2 (Production of an intermediate)

An amount of 59.4 g of 2-chloroethyl-trichloro-silane is dissolved in 750 ml of absolute diethyl ether; an addition is then made in the course of one hour at $-5°$ to $-10°$ of a mixture of 69.7 g of hexan-(1)-ol and 47.5 g of absolute pyridine dissolved in 250 ml of absolute ether. The mixture is subsequently stirred for 12 hours at room temperature; filtration is then performed and the filtrate concentrated in vacuo. After fractional distillation there is obtained 32.5 g of 2-chloroethyl-(dihexyloxychloro)-silane;

B.P.: 97 - 102°/0.001 Torr, $n_{20}^D = 1.4423$.

EXAMPLE 3 (Production of an intermediate)

An amount of 35.5 g of 2-chloroethyl-methyl-dichlorosilane is dissolved in 300 ml of absolute diethyl ether; an addition is made in the course of one hour at −5° to −10° of a mixture of 2.6 g of benzyl alcohol and 15.8 g of absolute pyridine dissolved in 100 ml of absolute ether. The mixture is stirred for 12 hours at room temperature; filtration is subsequently performed and the filtrate concentrated in vacuo. There is obtained 53.3 g of 2-chloroethyl-(methyl-benzyloxy-chloro)-silane; $n_{20}{}^D = 1.5123$.

EXAMPLE 4

A mixture of 30.3 g of triethylamine and 32.1 g of benzylamine is dissolved in 400 ml of absolute diethyl ether; an addition is made at −5° to −10° in the course of 1½ to 2 hours of 19.8 g of 2-chloroethyl-trichlorosilane dissolved in 100 ml of absolute ether. The mixture is stirred for 24 hours at 0° and for 12 hours at room temperature; filtration is then performed and the filtrate concentrated in vacuo. There is obtained 37 g of 2-chloroethyl-(tribenzylamino)-silane; $n_{20}{}^D = 1.5730$ Calculated: Si, 6.9%. Found: Si, 7.1%.

EXAMPLE 5

An amount of 13.2 g of 2-chloroethyl-(hexyloxy-dichloro)-silane is dissolved in 100 ml of absolute diethyl ether; additions are then made at −10°, in the course of 30 minutes, firstly of 12.4 g of benzylmercaptan and then of 7.9 g of absolute pyridine dissolved in 50 ml of absolute ether. The mixture is subsequently stirred for 2 hours at 0° and for 2 hours at room temperature and afterwards refluxed for 36 hours. Filtration is performed; the filtrate is quickly washed with ice cold water, dried, and concentrated in vacuo to obtain 23 g of 2-chloroethyl-(hexyloxy-dibenzylthio)-silane; $n_{20}{}^D = 1.5215$ Calculated: Si, 6.4%. Found: Si, 6.3%.

EXAMPLE 6 (Production of a starting material)

42.3 g of vinyl-methyl-dichlorosilane is cooled to −5° to 0°. Hydrogen bromide is then introduced at this temperature, with UV-irradiation, for a period of 30 to 40 minutes. After completion of the HBr-absorption, the solution is allowed to stand overnight in a nitrogen atmosphere at room temperature. There is obtained an amount of 61.6 g of the new compound 2-bromoethyl-(methyl-dichloro)-silane; B.P.: 94°– 96°/57 Torr.

Calculated: Si, 12.6%. Found: Si, 13.0%.

EXAMPLE 7 (Production of a starting material)

A mixture of 142.3 g of vinyl-methyl-dichlorosilane and 1 g of anhydrous AlCl₃ is cooled to −5° to 0°. Hydrogen chloride is introduced at this temperature, with UV-irradiation, for a period of 90 minutes. After completion of the ZHCl-absorption, the product is distilled at 0.1 Torr and at a bath temperature of at most 15° into a flask cooled with dry ice. There is obtained 177.5 g of the known 2-chloroethyl-(methyl-dichloro)-silane;B.P.: 82°– 84°/68 Torr.

Calculated: Si, 15.8. Found: Si, 16.4.

In analogous manner to these Examples compounds of formula I $$\begin{array}{c} A \\ | \\ B-Si-CH_2CH_2X \\ | \\ C \end{array} \quad (I)$$

of the following composition are produced:

| A | B | C |
|---|---|---|
| $R_1$—S— | $R_1$—S— | $R_1$—S— |
| $R_2$—N— | $R_2$—N— | $R_2$—N— |
| \| | \| | \| |
| $R_3$ | $R_3$ | $R_3$ |
| | $R_4$O— | $R_4$O— |
| | | $CH_3$ or —CH₂—  |

Table I

Compounds of formula Ia,
wherein $A = B = C = R_1-S-$
$(R_1-S-)_3 Si-CH_2-CH_2 X$ (Ia) and
Compounds of formula Ib,
wherein $A = B = R_1-S-$ and C is methyl
$(R_1-S-)_2 Si-CH_2-CH_2 X$ (Ib):
$\quad\quad\quad\quad |$
$\quad\quad\quad CH_3$

| | $A = R_1-S$ $R_1$ is: | $B = R_1S$ $R_1$ is: | C | X | Physical data |
|---|---|---|---|---|---|
| 1 | Ethyl | $=R_1$ | $= R_1-S$ | Cl | |
| 2 | Butyl | " | " | Cl | |
| 3 | Octyl | " | " | Cl | |
| 4 | Octyl | " | $CH_3$ | Cl | |
| 5 | Dodecyl | " | $R_1-S$ | Cl | |
| 6 | Octadecyl | " | " | Cl | |
| 7 | Octadecyl | " | $CH_3$ | Cl | |
| 8 | Methoxycarbonyl-ethyl | " | $R_1-S$ | Cl | |
| 9 | 3-Phenylpropyl | " | " | Cl | |
| 10 | Cyclohexyl | " | $CH_3$ | Br | |
| 11 | 2-Propenyl | " | $R_1-S$ | Cl | |
| 12 | Phenyl | " | " | Cl | |
| 13 | 4-Bromophenyl | " | $CH_3$ | Cl | |
| 14 | 4-Chlorophenyl | " | $CH_3$ | Cl | |
| 15 | 4-Chlorophenyl | " | $R_1-S$ | Cl | |
| 16 | 4-tert. Butylphenyl | " | $R_1-S$ | Cl | |
| 17 | 4-Bromo-3-methyl-phenyl | " | $CH_3$ | Cl | |
| 18 | 4-Methoxyphenyl | " | $R_1-S$ | Cl | |
| 19 | 4-Methoxyphenyl | " | $CH_3$ | Cl | |
| 20 | 3-Methylphenyl | " | $R_1-S$ | Br | |
| 21 | Benzyl | " | " | Cl | |
| 22 | Benzyl | " | $CH_3$ | Cl | |
| 23 | 4-Chlorobenzyl | " | $R_1-S$ | Br | |
| 24 | 4-Chlorobenzyl | " | $CH_3$ | | |
| 25 | 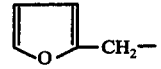 | " | $R_1-S$ | Cl | |

Table 2

Compounds of formula Ic
wherein $A = B = R_1-S-$ and $C = R_4O-$
$(R_1-S-)_2Si-CH_2-CH_2-X$ (Ic):
$\quad\quad\quad\quad |$
$\quad\quad\quad OR_4$

| | $A = R_1-S$ $R_1$ is: | $B = R_1S$ $R_1$ is: | $C = R_4O$ $R_4$ is: | X | Physical data |
|---|---|---|---|---|---|
| 26 | Ethyl | $=R_1$ | Ethyl | Cl | |
| 27 | Butyl | " | Butyl | Cl | |
| 28 | Butyl | " | Hexyl | Cl | $n_D{}^{20} = 1.4899$ |
| 29 | butyl | " | Octadecyl | Cl | |
| 30 | Butyl | " | Cyclohexyl | Cl | |

Table 2-continued

Compounds of formula Ic
wherein A = B = $R_1$—S— and C = $R_4$O—

$$(R_1-S-)_2\underset{\underset{OR_4}{|}}{Si}-CH_2-CH_2-X \quad (Ic):$$

| | A = $R_1$—S<br>$R_1$ is: | B = $R_1$S<br>$R_1$ is: | C = $R_4$O<br>$R_4$ is: | X | Physical data |
|---|---|---|---|---|---|
| 31 | Butyl | " | 3-Methylphenyl | Cl | |
| 32 | Butyl | " | ⟨tetrahydropyranyl⟩-CH₂— | Cl | |
| 33 | Benzyl | " | Hexyl | Cl | $n_{20}^D = 1.5215$ |
| 34 | Benzyl | " | Benzyl | Cl | |
| 35 | 4-Chlorobenzyl | " | Benzyl | Cl | |
| 36 | 4-Chlorobenzyl | " | Octyl | Br | |
| 37 | 3,4-Dichlorophenyl | " | Octyl | Cl | |
| 38 | 4-tert. Butylphenyl | " | Octyl | Cl | |
| 39 | 4-Methoxyphenyl | " | Octyl | Cl | |
| 40 | 3-Phenylpropyl | " | Benzyl | Br | |
| 41 | Octyl | " | Dodecyl | Br | |
| 42 | ⟨furyl⟩-CH₂— | " | ⟨tetrahydrofuryl⟩-CH₂— | Cl | |
| 43 | Octyl | " | 3-Hexynyl | Cl | |
| 44 | 3,4-Dimethylphenyl | " | Ethyl | Cl | |

Table 3

Compounds of formula Id
wherein A = $R_1$—S— and B = C = $R_4$O—

$$R_1-S-\underset{\underset{(OR_4)_2}{|}}{Si}-CH_2CH_2-X$$

| | A = $R_1$S<br>$R_1$ is: | B = $R_4$—O—<br>$R_4$ is: | C = $R_4$—O—<br>$R_4$ is: | X | Physical data |
|---|---|---|---|---|---|
| 45 | Benzyl | 2-Ethoxyethyl | =$R_4$ | Cl | |
| 46 | Benzyl | 2-Butenyl | " | Cl | |
| 47 | Benzyl | 2-Propynyl | " | Cl | |
| 48 | Benzyl | Hexyl | " | Cl | $n_{20D} = 1.4608$ |
| 49 | Benzyl | 3-Hexynyl | " | Cl | |
| 50 | Benzyl | 3-Phenyl-2-propenyl | " | Cl | |
| 51 | Butyl | Cyclohexylmethyl | " | Br | |
| 52 | Butyl | 3-Methylphenyl | " | Cl | |
| 53 | Butyl | Ethoxycarbonylmethyl | " | Cl | |
| 54 | Butyl | ⟨tetrahydropyranyl⟩-CH₂— | " | Cl | |
| 55 | Ethyl | 2,4-Dichlorobenzyl | " | Cl | |
| 56 | Ethyl | ⟨thienyl⟩-CH₂— | " | Cl | |
| 57 | Ethyl | ⟨tetrahydrofuryl⟩-CH₂— | " | Cl | |
| 57a | Butyl | Hexyl | " | Cl | $n_D^{20} = 1.4527$ |

Table 4

Compounds of formula Ie
wherein A = $R_1$—S—, B = $R_4$—O— and C is methyl $$R_1-S-\underset{\underset{OR_4}{|}}{\overset{\overset{CH_3}{|}}{Si}}-CH_2CH_2X \quad (Ie)$$

| | A = $R_1$—S<br>$R_1$ is: | B = $R_4$O<br>$R_4$ is: | C | X | Physical data |
|---|---|---|---|---|---|
| 58 | Ethyl | Ethyl | CH₃ | Cl | |
| 59 | " | Butyl | " | Cl | |
| 60 | " | Octyl | " | Cl | |
| 61 | " | Dodecyl | " | Cl | |
| 62 | " | Octadecyl | " | Cl | |
| 63 | Butyl | 6-Chlorohexyl | " | Cl | |
| 64 | " | 2-Butyloxyethyl | " | Cl | |
| 65 | " | 2-Ethylthioethyl | " | Cl | |
| 66 | " | Benzyl | " | Cl | |
| 67 | " | 2-Allyloxyethyl | " | Br | $n_D^{20} = 1.4466$ |
| 68 | Octyl | 2-Phenoxyethyl | " | Cl | |
| 69 | " | 2-Butenyl | " | Cl | |
| 70 | " | 2-Propynyl | " | Cl | |
| 71 | " | 3-Hexynyl | " | Br | |
| 72 | Benzyl | Cyclohexylmethyl | " | Cl | |
| 73 | " | Cyclohexyl | " | Cl | |
| 74 | " | 3-Phenyl-2-propenyl | " | Cl | |
| 75 | " | Benzyl | " | Cl | |
| 76 | " | Phenyl | " | Br | $n_{20}^D = 1.5353$ |
| 77 | Butyl | 3-Chlorophenyl | " | Cl | |
| 78 | 4-Chlorobenzyl | Octyl | " | Cl | |
| 79 | 4-Bromophenyl | 4-Bromophenyl | " | Cl | |
| 80 | Cyclohexyl | Cyclohexyl | " | Br | |
| 81 | 4-Methoxyphenyl | 3,4-Dimethylphenyl | " | Cl | |
| 82 | 3-Methylphenyl | Octyl | " | Cl | |
| 83 | 2-Propenyl | Octyl | " | Cl | |
| 84 | 3-Phenylpropyl | 3-Phenylpropyl | " | Cl | |

Table 5

Compounds of formula If,
wherein A = B = C =

$$-N-R_2 \ (R_2-N-)_3 \ Si-CH_2CH_2X \ (If) \text{ and}$$
$$\ \ \ |\ \ \ \ \ \ \ \ \ \ \ \ \ |$$
$$\ \ R_3 \ \ \ \ \ \ \ \ \ R_3$$

Compounds of formula Ig, wherein A = B = N—R$_2$ and C is methyl
$\ \ \ \ \ \ \ \ \ \ \ \ \ \ \ \ \ \ \ \ \ \ \ \ \ \ \ \ \ \ \ |$
$\ \ \ \ \ \ \ \ \ \ \ \ \ \ \ \ \ \ \ \ \ \ \ \ \ \ \ \ \ \ \ R_3$ $$(R_2-N-)_2 \ Si-CH_2-CH_2X \ (Ig)$$
$$\ \ \ \ \ \ \ |\ \ \ \ \ \ \ \ \ |$$
$$\ \ \ \ \ R_3 \ \ \ \ CH_3$$

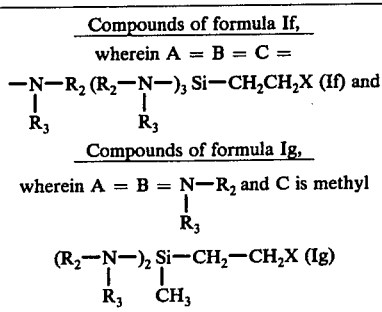

A =

|  | R$_2$ | R$_3$ | B | C | X | Physical data |
|---|---|---|---|---|---|---|
| 85 | Ethyl | Ethyl | =A | =A | Cl | |
| 86 | H | Butyl | " | " | Cl | |
| 87 | Butyl | Butyl | " | CH$_3$ | Cl | |
| 88 | H | Octyl | " | =A | Cl | $n_{20}^D = 1.4630$ |
| 89 | " | " | " | CH$_3$ | Cl | $n_{20}^D = 1.4581$ |
| 90 | " | Dodecyl | " | =A | Cl | $n_{20}^D = 1.4615$ |
| 91 | " | Octadecyl | " | CH$_3$ | Cl | M.P. 60 – 65° |
| 92 | " | 2-Propenyl | " | CH$_3$ | Cl | $n_D^{22,5} = 1.4778$ |
| 93 | " | 9-Octadecenyl | " | CH$_3$ | Cl | |
| 94 | " | 2-Propynyl | " | =A | Cl | |
| 95 | " | 1,2,2-Trimethylpropenyl | " | CH$_3$ | " | |
| 96 | " | 1-Methylhexyl | " | =A | " | |
| 97 | " | 1,3-Dimethylbutyl | " | CH$_3$ | " | |
| 98 | " | 1-Methylpropyl | " | =A | " | |
| 99 | " | Pentyl | " | " | " | |
| 100 | " | Decyl | " | " | " | |
| 101 | " | 2-Ethylhexyl | " | " | " | |
| 102 | " | Hexadecyl | " | CH$_3$ | " | |
| 103 | " | Cyclohexyl | " | CH$_3$ | " | $n_D^{20} = 1,4925$ |
| 104 | " | Cyclohexylmethyl | " | =A | " | |
| 105 | " | 2-Methyoxyethyl | " | " | " | |
| 106 | " | 3-Isopropoxypyropyl | " | " | " | |
| 107 | " | 2,2-Diphenylethyl | " | CH$_3$ | " | |
| 108 | " | Benzyl | " | =A | " | M.P. 55 = 65° |
| 109 | " | Benzyl | " | CH$_3$ | " | $n_{20}^D = 1.5394$ |
| 110 | " | 4-Chlorobenzyl | " | =A | " | |
| 111 | Methyl | Benzyl | " | CH$_3$ | " | |
| 112 | H | 3-Chlorobenzyl | " | " | " | |
| 113 | " | 3,4-Dichlorobenzyl | " | " | " | |
| 114 | " | 4-Methoxybenzyl | " | " | " | |
| 115 | " | Phenyl | " | " | " | $n_D^{22} = 1.5850$ |
| 116 | " | 4-Bromophenyl | " | " | " | $n_D^{22} = 1.6140$ |
| 117 | " | 4-Methoxyphenyl | " | =A | " | |
| 118 | " | 3-Chlorophenyl | " | " | " | |
| 119 | " | 4-Methylthiophenyl | " | CH$_3$ | " | |
| 120 | " | 3-Methylphenyl | " | CH$_3$ | " | $n_D^{22} = 1,5748$ |
| 121 | " | ⟨pyridinyl⟩—CH$_2$CH$_2$— | " | CH$_3$ | " | |
| 122 | " | ⟨pyridinyl⟩—CH$_2$— | " | " | " | $n_D^{22} = 1.5690$ |
| 123 | " | ⟨furanyl⟩—CH$_2$— | " | " | " | $n_D^{22} = 1.5134$ |
| 124 | " | ⟨tetrahydrofuranyl⟩—CH$_2$— | " | =A | " | |
| 125 | " | 2-Propenyl | " | " | " | $n_D^{22} = 1.4929$ |

Table 6

Compounds of formula Ih wherein $A = -N-R_2$, $B = OR_4$, $\underset{R_3}{|}$

C is methyl or Benzyl (=$R_5$)

$$R_2-\underset{\underset{R_3}{|}}{\overset{\overset{R_5}{|}}{N}}-\underset{\underset{OR_4}{|}}{Si}-CH_2CH_2X \quad (Ih)$$

| | A = $R_2R_3N$ | | B = $R_4O$ | C = $R_5$ | | |
|---|---|---|---|---|---|---|
| | $R_2$ | $R_3$ | $R_4$ is: | $R_5$ | X | $n_D^{23}$ |
| 126 | H | $CH_3$ | Benzyl | $CH_3$ | CL | 1.5228 |
| 127 | H | 2-methoxy-ethyl | " | " | Cl | 1.5037 |
| 128 | H | Pyridyl-(3) | " | " | Cl | 1.5450 |
| 129 | H | Phenyl | " | " | Cl | 1.5589 |
| 130 | H | Tetrahydro-furfuryl | " | Benzyl | Cl | 1.5342 |
| 131 | H | $CF_3$ | " | " | Cl | 1.5347 |
| 132 | H | Decyl | " | " | Cl | 1.5186 |
| 133 | H | 9-octadecenyl | " | " | Cl | 1.5087 |

We claim:
1. A β-halogenoethyl-silane of formula I

$$X-CH_2-CH_2-\underset{\underset{C}{|}}{\overset{\overset{A}{|}}{Si}}-B \quad (I)$$

wherein

A represents a radical $-S-R_1$ or $$-N\underset{R_3}{\overset{R_2}{<}},$$

B represents a radical $-SR_1$, $$-N\underset{R_3}{\overset{R_2}{<}}$$

or $-OR_4$,

C represents a radical $-SR_1$, $$-N\underset{R_3}{\overset{R_2}{<}},$$

$-OR_4$ the methyl or benzyl group, and

X represents chlorine or bromine,
whereby the radical $R_1$ represents $C_1-C_{18}$ alkyl; $C_1-C_{18}$ alkyl substituted by $C_1-C_8$ alkoxycarbonyl, phenyl or $C_3-C_{12}$ cycloalkyl; $C_3-C_{18}$ alkenyl; $C_3-C_8$ alkynyl; $C_3-C_{12}$ cycloalkyl; $C_3-C_{12}$ cycloalkenyl; phenyl optionally mono- or polysubstituted by $C_1-C_8$ alkyl, $C_1-C_8$ alkoxy, $C_1-C_8$ alkylthio or halogen; and benzyl optionally mono- or polysubstituted by $C_1-C_8$ alkyl, $C_1-C_8$ alkoxy, $C_1-C_8$ alkylthio or halogen; $R_3$ represents $C_1-C_{18}$ alkyl which can be substituted by $C_1-C_8$ alkoxy, $C_1-C_8$ alkylthio, phenyl or $C_3-C_{12}$ cycloalkyl; $C_3-C_{12}$ cycloalkyl; $C_3-C_{12}$ cycloalkenyl; $C_3-C_{18}$ alkenyl, $C_3-C_8$ alkynyl; phenyl optionally mono- or polysubstituted by $C_1-C_8$ alkyl, $C_1-C_8$ alkoxy, $C_1-C_8$ alkylthio or halogen; and benzyl optionally mono- or polysubstituted by $C_1-C_8$ alkyl, $C_1-C_8$ alkyloxy, $C_1-C_8$ alkylthio or halogen; $R_2$ represents hydrogen or the same as $R_3$; $R_4$ represents $C_1-C_{18}$ alkyl; $C_1-C_{18}$ alkyl substituted by halogen, $C_1-C_8$ alkoxy $C_1-C_8$ alkoxyalkoxy, $C_3-C_6$ alkenyloxy, phenoxy, $C_3-C_{12}$ cycloalkyl, $C_1-C_8$ alkylthio or $C_1-C_8$ alkoxycarbonyl; $C_3-C_{18}$ alkenyl; $C_3-C_{18}$ halogenoalkenyl; $C_3-C_8$ alkynyl; $C_3-C_{12}$ cycloalkyl; $C_3-C_{12}$ cycloalkenyl; phenyl radicals optionally mono- or polysubstituted by cyano, nitro, $C_1-C_8$ alkyl, $C_1-C_6$ halogenoalkyl, $C_1-C_8$ alkoxy, $C_1-C_8$ alkylthio, or $C_1-C_8$ alkoxycarbonyl; and benzyl radicals optionally mono- or polysubstituted by $C_1-C_8$ alkyl, $C_1-C_8$ alkoxy or halogen.

2. β-halogenoethyl-silanes according to claim 1 of formula Ia $$(R_1-S-)_3Si-CH_2-CH_2X \quad (Ia)$$

wherein $R_1$ and X have the meaning given in claim 1.

3. Halogeno-methyl-silanes according to claim 1 of formula Ib $$(R_1-S-)_2\underset{\underset{CH_3}{|}}{Si}-CH_2-CH_2X \quad (Ib)$$

wherein $R_1$ and X have the meaning given in claim 1.

4. Halogenoethyl-silanes according to claim 1 of formula Ic $$(R_1-S-)_2\underset{\underset{O-R_4}{|}}{Si}-CH_2-CH_2X \quad (Ic)$$

wherein $R_1$, $R_4$ and X have the meaning given in claim 1.

5. Halogenoethyl-silanes according to claim 1 of the formula Id $$R_1-S-\underset{\underset{(O-R_4)_2}{|}}{Si}-CH_2-CH_2X \quad (Id)$$

wherein $R_1$, $R_4$ and X have the meaning given in claim 1.

6. Halogenoethyl-methyl-silanes according to claim 1 of the formula Ie $$R_1-S-\underset{\underset{O-R_4}{|}}{\overset{\overset{CH_3}{|}}{Si}}-CH_2-CH_2X \quad (Ie)$$

wherein $R_1$, $R_4$ and X have the meaning given in claim 1.

7. Halogenoethyl-silanes according to claim 1 of the formula I f $$(R_2-\underset{\underset{R_3}{|}}{N}-)_3Si-CH_2-CH_2X \quad (If)$$

wherein $R_2$ and $R_3$ have the meaning given in claim 1.

8. Halogenoethyl-methyl silanes according to claim 1 of the formula Ig

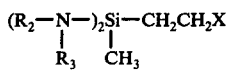    (Ig)

wherein $R_2$ and $R_3$ have the meaning given in claim 1.

9. Halogenoethyl-silanes according to claim 1 of the formula Ih

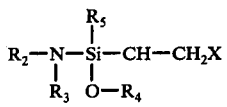    (Ih)

wherein $R_2$, $R_3$ and $R_4$ have the meaning given in claim 1 and $R_5$ represents a methyl or benzyl radical.

10. The halogenoethyl-silane according to claim 1

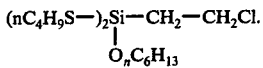

11. The halogenoethyl-silane according to claim 1

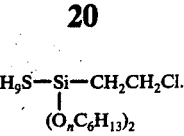

12. The halogenoethyl-methyl-silane according to claim 1

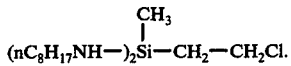

13. The halogenoethyl-methyl-silane according to claim 1

$$(nC_8H_{17}NH-)_2\overset{\overset{\displaystyle CH_3}{|}}{Si}-CH_2-CH_2Cl.$$

14. The halogenoethyl-methyl-silane according to claim 1

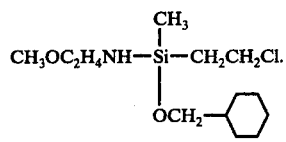

* * * * *